(12) United States Patent
Shibuya et al.

(10) Patent No.: US 7,912,276 B2
(45) Date of Patent: Mar. 22, 2011

(54) METHOD AND APPARATUS FOR DETECTING PATTERN DEFECTS

(75) Inventors: Hisae Shibuya, Chigasaki (JP); Akira Hamamatsu, Yokohama (JP); Yuji Takagi, Kamakura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/755,453

(22) Filed: Apr. 7, 2010

(65) Prior Publication Data

US 2010/0195896 A1   Aug. 5, 2010

Related U.S. Application Data

(63) Continuation of application No. 11/319,271, filed on Dec. 29, 2005, now Pat. No. 7,720,275.

(30) Foreign Application Priority Data

Mar. 24, 2005   (JP) .................................. 2005-085381

(51) Int. Cl.
*G06K 9/00* (2006.01)
*G06K 9/62* (2006.01)
(52) U.S. Cl. ....................................... 382/149; 382/224
(58) Field of Classification Search .......... 382/141–149, 382/159, 224, 309; 348/92, 125
See application file for complete search history.

(56) References Cited

U.S. PATENT DOCUMENTS

| 6,792,366 | B2 | 9/2004 | Hosoya et al. |
| 6,876,445 | B2 | 4/2005 | Shibuya et al. |
| 6,922,482 | B1 | 7/2005 | Ben-Porath |
| 7,332,359 | B2 | 2/2008 | Hamamatsu et al. |
| 2001/0042705 | A1 | 11/2001 | Nakagaki et al. |
| 2002/0122174 | A1 | 9/2002 | Hamamatsu et al. |
| 2004/0064269 | A1 | 4/2004 | Shibuya et al. |
| 2004/0218806 | A1 | 11/2004 | Miyamoto et al. |

FOREIGN PATENT DOCUMENTS

| JP | 2002-257533 | 9/2002 |
| JP | 2003-59984 | 2/2003 |
| JP | 2003-240731 | 8/2003 |
| JP | 2004-47939 | 2/2004 |
| JP | 2004-117229 | 4/2004 |

*Primary Examiner* — Daniel G Mariam
(74) *Attorney, Agent, or Firm* — Antonelli, Terry, Stout & Kraus, LLP

(57) ABSTRACT

With the objective of achieving defect kind training in a short period of time to teach classification conditions of defects detected as a result of inspecting a thin film device, according to one aspect of the present invention, there is provided a visual inspection method, and an apparatus therefor, comprising the steps of: detecting defects based on inspection images acquired by optical or electronic defect detection means, and at the same time calculating features of the defects; and classifying the defects according to classification conditions set beforehand, wherein said classification condition setting step further includes the steps of: collecting defect features over a large number of defects acquired beforehand from the defect detection step; sampling defects based on the distribution of the collected defect features over the large number of defects; and setting defect classification conditions based on the result of reviewing the sampled defects.

16 Claims, 10 Drawing Sheets

RANDOM SAMPLING

FEATURE SPACE EQUALIZATION SAMPLING

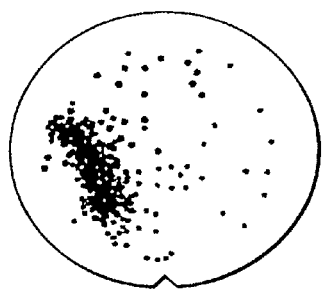
FIG. 10A
DENSELY
LOCATED DEFECTS
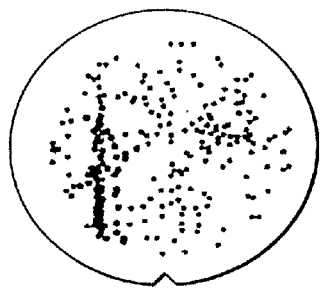
FIG. 10B
LINEAR DEFECTS
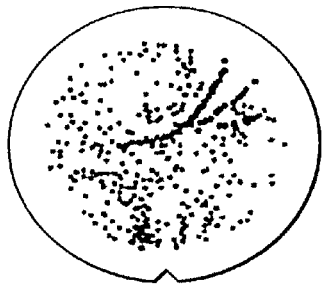
FIG. 10C
CIRCULAR ARC
SHAPED DEFECTS
FIG. 11
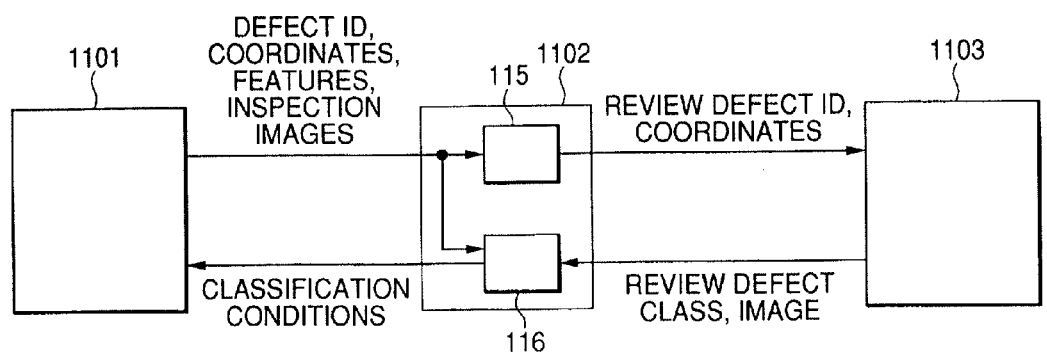

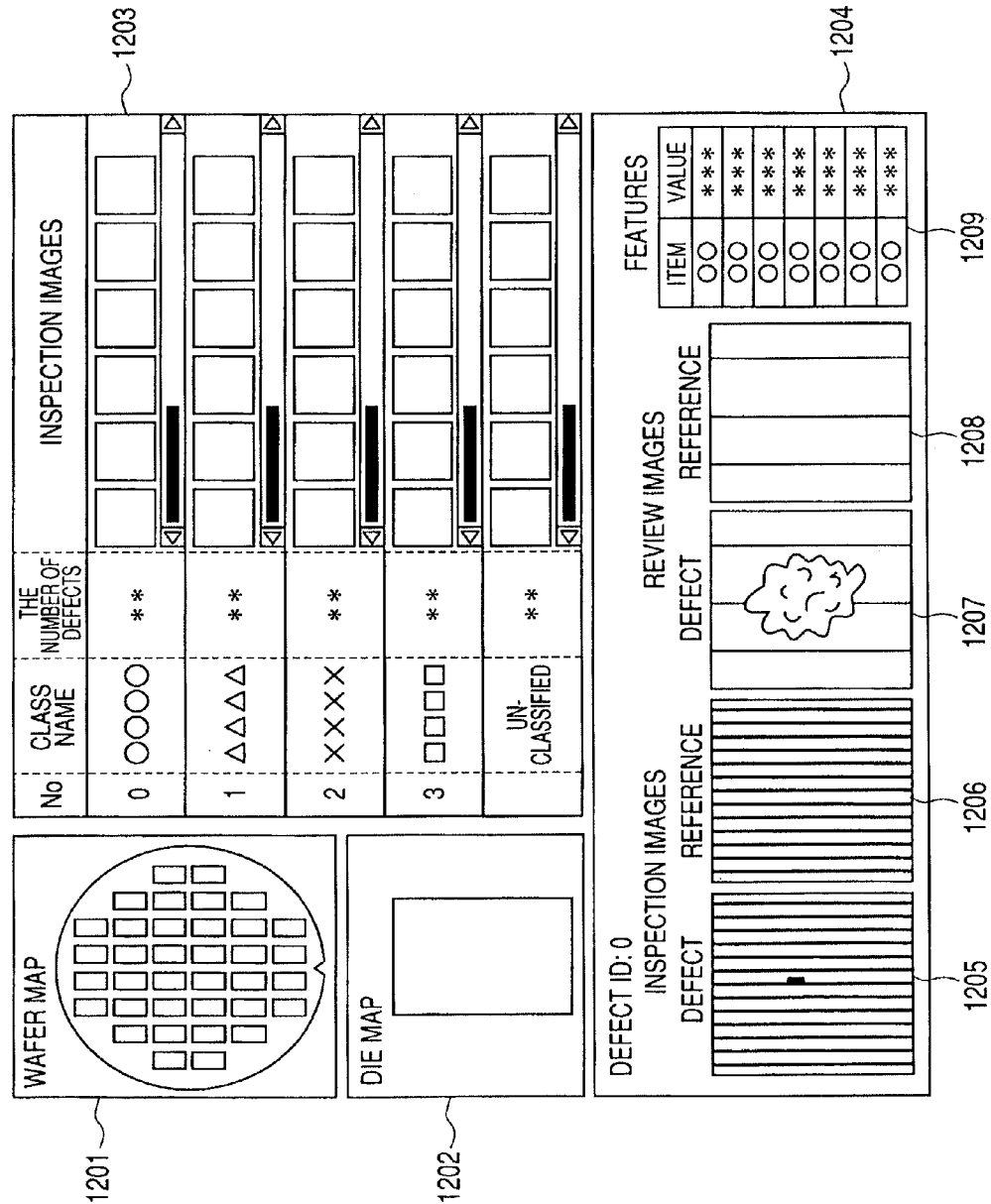

METHOD AND APPARATUS FOR DETECTING PATTERN DEFECTS

CLAIM OF PRIORITY

This application is a continuation of application Ser. No. 11/319,271, filed on Dec. 29, 2005 now U.S. Pat. No. 7,720,275, now allowed, which claims the benefit of Japanese Application No. 2005-085381, filed Mar. 24, 2005 in the Japanese Patent Office, the disclosures of which are incorporated herein by reference.

BACKGROUND OF THE INVENTION

The present invention relates to a visual inspection method, and an apparatus, for detecting defects including minute pattern defects and particles on the basis of an image of an object, which has been acquired by use of lamp light, a laser beam, an electron beam, or the like, and for classifying the defects, the visual inspection method and apparatus being targeted for thin film devices including a semiconductor wafer, TFT, and a photo mask. In particular, the present invention relates to a visual inspection method and an apparatus that are suitable for visual inspection of a semiconductor wafer.

Thin film devices such as a semiconductor wafer, a liquid crystal display, and a magnetic head of a hard disk are manufactured through many fabrication processes. In the manufacturing of such thin film devices, with the objective of improving and stabilizing yields, visual inspection is performed for each series of processes. In the visual inspection, defects such as a pattern defect and a foreign particle are detected on the basis of an image acquired by use of lamp light, a laser beam, an electron beam, or the like. At the same time, there is also a case where defects are classified on the basis of features of defects such as the brightness and the size. For example, Japanese Patent Laid-Open No. 2002-257533 (corresponding to U.S. application Ser. No. 10/050,776) discloses an inspection apparatus that classifies defects into particles which are convex defects and scratches which are concave defects according to a difference in intensity between scattered light by vertical lighting and scattered light by oblique lighting. When defect classification conditions of the inspection apparatus having such a defect classification function are determined, it is necessary to instruct classes into which defects are classified by reviewing, and to determine the relationship between a feature and a class. In the above example, the classes into which defects are classified are a particle class and a scratch class. Accordingly, it is assumed that the intensity of scattered light at the time of vertical lighting and the intensity of scattered light at the time of oblique lighting are features. Then, on the basis of a two-dimensional scatter diagram, a discrimination line is manually set.

Incidentally, other than the technique disclosed in the Japanese Patent Laid-Open No. 2002-257533 described above, techniques which are known as the background art pertaining to the present invention include: the technique disclosed in Japanese Patent Laid-Open No. 2004-47939; the technique disclosed in Japanese Patent Laid-Open No. 2003-59984 (corresponding to U.S. Pat. No. 6,876,445 B2); the technology disclosed in Japanese Patent Laid-Open No. 2004-117229 (corresponding to U.S. application Ser. No. 10/672,010); and the technique disclosed in the 13th workshop on automation of visual inspection, pp. 99-104 (December, 2001).

As far as the visual inspection of semiconductor wafers are connected, as a result of the miniaturization of patterns, the size of a target defect to be detected becomes smaller, and the number of detected defects increases to a level ranging from several thousand to tens of thousands. Therefore, because it is practically impossible to review all defects, it is necessary to sample defects, the number of which is from several tens to several hundreds, before the sampled defects are reviewed. However, when defects are sampled at random, if a defect occurrence ratio deviates from the usual, the same kind of defects are mainly selected, resulting in the unclear relationship between a feature and a class. Accordingly, classification conditions cannot be correctly set, which was a problem to be solved.

SUMMARY OF THE INVENTION

The present invention has been made to solve the above mentioned problem, and an object of the present invention is to provide a visual inspection method, and an apparatus, which are capable of correctly setting classification conditions even if a defect occurrence ratio deviates from the usual.

In order to achieve the above mentioned object, according to one aspect of the present invention, there is provided a visual inspection method, and an apparatus therefor, comprising the steps of: on the basis of inspection images acquired by optical or electronic defect detection means, detecting defects by comparison inspecting, and at the same time calculating features of the defects; and classifying the defects according to classification conditions set beforehand by classification condition setting means; wherein the classification condition setting means further comprises the steps of: collecting defect features cover a large number of defects acquired beforehand from the defect detection means; sampling defects on the basis of the distribution of the collected defect features over the large number of defects; and setting defect classification conditions on the basis of the result of reviewing the sampled defects.

According to another aspect of the present invention, there is provided a visual inspection method, and an apparatus therefor, comprising the steps of: setting classification conditions beforehand; detecting defects by using inspection images acquired by imaging a target substrate, and calculating features of the detected defects; and classifying the defects on the basis of the classification conditions set beforehand in the classification condition setting step by using the defect features calculated in the defect detection step; wherein: the classification condition setting step further includes the steps of: detecting a large number of defects by using inspection images acquired by imaging the target substrate, and calculating feature of each defect over the large number of detected defects, and collecting the calculated feature of the each defect over the large number of defects to store the collected features; creating defect feature distribution indicating defect occurrence distribution based on the defect feature of the each defect over the large number of defects collected in the collection step, and performing sampling review defects based on the created defect feature distribution; and giving at least defect classes to a plurality of review defects by reviewing for the review defects sampled in the defect sampling step; wherein the defect classes of the review defects given in the review step for the features of the review defects collected in the collection step, are set as training (teaching) data of the classification conditions.

In addition, according to the present invention, in the defect sampling step, a desired one-dimensional feature histogram over a large number of defects is created as the defect feature distribution, and sampling is performed so that in the created desired one-dimensional feature histogram, number of samples from each of sections into which the one-dimensional feature histogram is divided with respect to the features becomes roughly equal with the sections where section in where sampling defect doesn't become to exist is excepted.

Moreover, according to the present invention, in the defect sampling step, a desired two-dimensional feature space over a large number of defects is created as the defect feature distribution, and the sampling is performed so that in the created desired two-dimensional feature space, which is divided into cells of a lattice with respect to the features, number of samples included in each cell of the lattice becomes roughly equal with the exception of cells of the lattice where cell of the lattice in where the sampling defect doesn't become to exist is excepted.

Further, according to the present invention, the defect sampling step further includes the steps of: creating a plurality of feature histograms over a large number of defects as the defect feature distribution; and displaying the plurality of feature histograms created in the creation step; and selecting one feature histogram from among the plurality of feature histograms displayed in the displaying step, and performing sampling so that number of samples from each of feature sections which have been freely set in the selected one of the feature histograms becomes roughly equal with feature sections where feature section in where the sampling defect doesn't become to exist is excepted.

Still further, according to the present invention, in the collection step, the collected defect feature of the each defect include feature based on defect images, and feature based on position coordinates of defects.

According to still another aspect of the present invention, there is provided a visual inspection method, and an apparatus therefor, comprising the steps of: setting classification conditions beforehand; detecting defects by using inspection images acquired by imaging a target substrate, and calculating features and position information of the detected defects; and classifying the defects in accordance with the classification conditions set beforehand in the classification condition setting step by using the features and the position information of the defects calculated in the defect detection step; wherein: the classification condition setting step further includes the steps of: detecting a large number of defects by using inspection images acquired by imaging a target substrate, and calculating features and position information of the large number of detected defects, and collecting the calculated features and position information of each defect over the large number of defects; extracting clusters on the basis of the position information of the large number of defects to store the collected feature and position information of the each defect; and for defects except the extracted clusters, creating defect feature distribution indicating defect occurrence distribution based on the defect feature of each defect over the large number of defects collected in the collection step, and performing sampling review defects based on the created defect feature distribution; and giving at least defect classes to a plurality of review defects by reviewing for the review defects sampled in the defect sampling step; wherein for the defects except the extracted clusters, the defect classes of the review defects given in the review step for the features of the review defects collected in the collection step, are set as training data of the classification conditions.

According to the present invention, it is possible to equally review and teach defects of each class irrespective of an occurrence ratio of them by performing sampling of defects on the basis of the distribution of defect features. Therefore, it is possible to correctly keep track of the relationship between a defect class and a feature only with a small number of reviews, and thereby to set classification conditions that will produce correct results.

These and other objects, features and advantages of the invention will be apparent from the following more particular description of preferred embodiments of the invention, as illustrated in the accompanying drawings.

BRIEF DESCRIPTION OF THE DRAWINGS

FIG. 10A is a diagram illustrating an example of a wafer map in which densely located defects exist, FIG. 10B is a diagram illustrating an example of a wafer map in which linear defects exist, and FIG. 10C is a diagram illustrating an example of a wafer map in which circular arc shaped defects exist;

FIG. 11 is a diagram illustrating one embodiment of a system configuration that includes a classification condition setting unit; and FIG. 12 is a diagram illustrating an embodiment of a GUI through which review images are inputted and manually classified.

DETAILED DESCRIPTION OF THE PREFERRED EMBODIMENTS

Embodiments of a visual inspection method and an apparatus according to the present invention will be described with reference to drawings.

First Embodiment

First of all, a first embodiment of a visual inspection method and an apparatus according to the present invention will be described in detail with reference to FIGS. 1 through 8.

Figure 1:
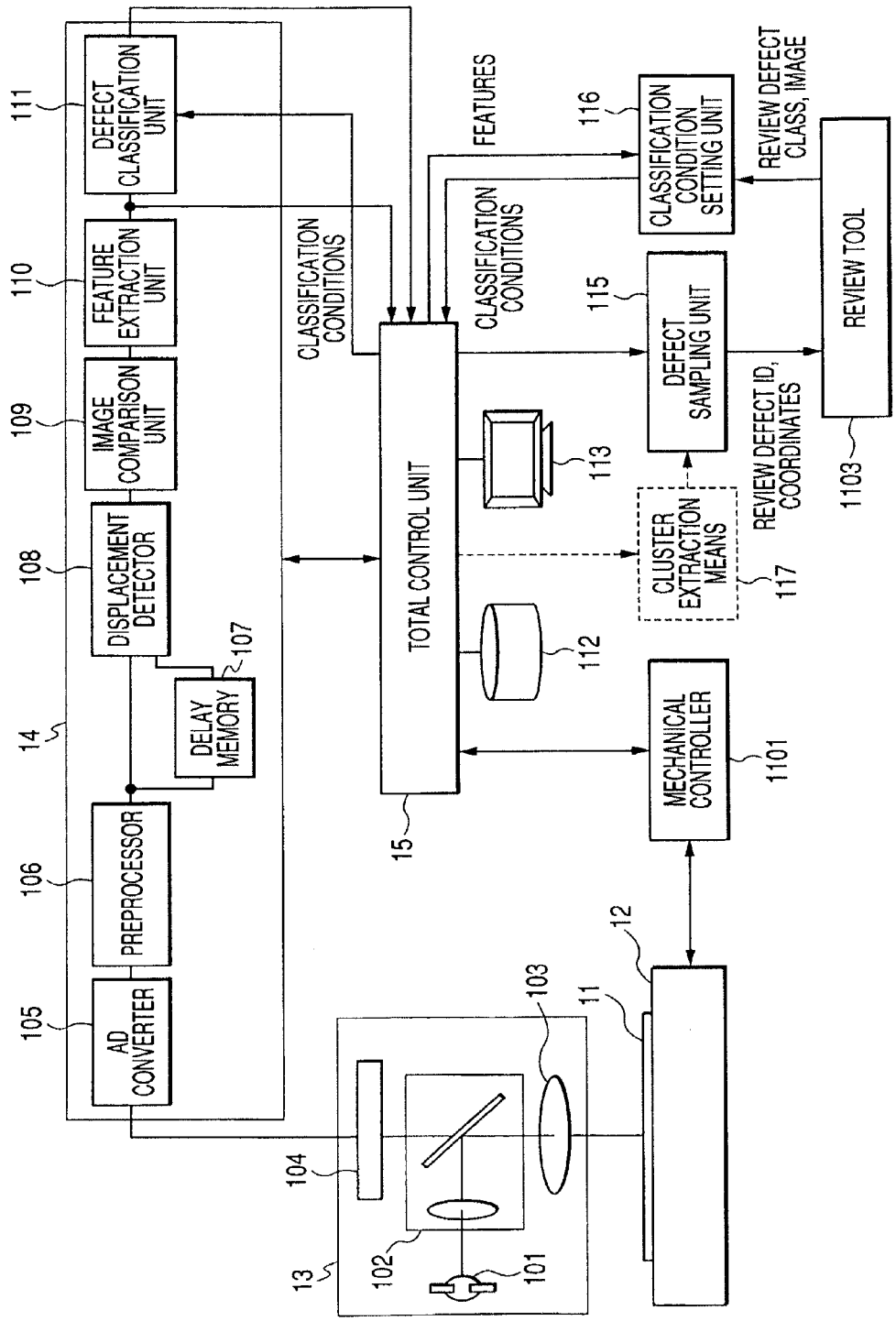
FIG. 1 is a diagram schematically illustrating a configuration of a visual inspection apparatus according to one embodiment.

A first embodiment of an optical visual inspection apparatus targeted for semiconductor wafers will be described. FIG. 1 is a diagram illustrating a configuration of an optical visual inspection apparatus according to the first embodiment of the present invention. The optical visual inspection apparatus is configured to include a stage 12 to place a target substrate 11 such as a semiconductor wafer thereon and to be moved, and a detector 13. The detector 13 comprises: a light source 101 emitted a light beam for irradiating a illumination light beam onto the target substrate 11; an illumination optical system 102 for condensing the light beam emitted from the light source 101; an objective lens 103 for irradiating the target substrate 11 with the illumination light beam condensed by the illumination optical system 102 and for imaging an optical image obtained by reflecting from the target substrate 11; and an image sensor 104 for converting the focused optical image into an image signal in response to the brightness. Reference numeral 14 denotes an image processor that detects a defect candidate on the target wafer by use of the image detected by the detector 13.

For example, as described in Japanese Patent Laid-Open No. 2002-257533, the light source 101 includes a plurality of light sources each emitting an UV light beam, or a DUV light beam that has different wavelength in. The illumination optical system 102 includes: a high angle illumination (vertical lighting) optical system that irradiates an object to be inspected with the UV light beam or the DUV light beam, which has been emitted from one of the light sources, from a high angle direction which is a normal line direction or approximates to the normal line direction with respect to a surface of the object to be inspected; and a low angle illumination (oblique lighting) optical system that irradiates an object to be inspected with the UV light beam or the DUV light beam, which has been emitted from another light source, from a low angle direction angular to the surface of the object to be inspected. The image sensor 104 includes a plurality of sensors, one of which is used for high angle illumination, and the other of which is used for low angle illumination. A beam splitter is placed between the objective lens 103 and the image sensor 104. Incidentally, by making a position to be irradiated at a high angle differ from a position to be irradiated at a low angle in a visual field of the objective lens 103, it is possible to make a wavelength of a high angle illumination light beam coincide with that of a low angle illumination light beam. However, it is necessary to adjust a light receiving surface of each of the image sensors so as to accommodate differences in positions to be irradiated on the surface of the object to be inspected.

The image processor 14 comprises: an AD converter 105 for converting, into a digital signal, an input signal coming from the image sensor 104 of the detector 13; a preprocessor 106 for performing image correction of the digital signal that has been analog-to-digital converted, the image correction including shading correction and darkness level correction; a delay memory 107 for storing, as a reference image signal, a digital signal to be compared; a displacement detector 108 for detecting the amount of displacement between the digital signal (detected image signal) detected by the detector 13 and the reference image signal stored in the delay memory 107; an image comparison unit 109 for comparing a detected image f (x, y), which is aligned on the basis of the amount of displacement detected by the displacement detector 108, with an image signal of a reference image g (x, y), and then for outputting, as a defect candidate, part whose difference value sub (x, y) is larger than a specific threshold value Th; a feature extraction unit 110 for calculating position coordinates, and a feature, of the defect candidate; and a defect classification unit 111 for classifying a defect on the basis of the feature.

A total control unit 15 is configured to include a CPU (not illustrated) that performs various kinds of control. A storage device 112 and a user interface 113 are connected to the total control unit 15. The storage device 112 stores an ID (including position coordinates) of a defect candidate calculated by the feature extraction unit 110, a feature of the defect candidate, an inspection image of the defect candidate, and the like.

The user interface 113 accepts a request by a user to change an inspection parameter, and displays information about a detected defect. A mechanical controller 1101 drives and controls the stage 12 on the basis of a control instruction sent from the total control unit 15. It is to be noted that, although not illustrated, the image processor 14, the detector 13, and the like, are also driven and controlled by instructions sent from the total control unit 15.

The total control unit (collection unit) 15 is required to collect, in advance, position coordinate information of each defect, and features of each defect, over a large number of defects acquired from the feature extraction unit 110, and then to store them in the storage device 112. As a result, a defect sampling unit 115 can select review defects on the basis of the position coordinate information of each defect, and the features of each defect, over the large number of defects acquired from the total control unit (collection unit) 15. Moreover, a classification condition setting unit 116 can set beforehand classification conditions used for the defect classification unit 111 on the basis of the feature of each review defect acquired through the total control part 15 and the result of reviewing each review defect acquired from the review tool 1103. Thus, classification condition setting means comprises: the defect sampling unit 115; the classification condition setting unit 116; and input means for inputting the review result from the review tool 1103, including the total control unit (collection unit) 15.

Next, a defect detection method carried out by a visual inspection apparatus shown in FIG. 1 will be described.

Figure 2:
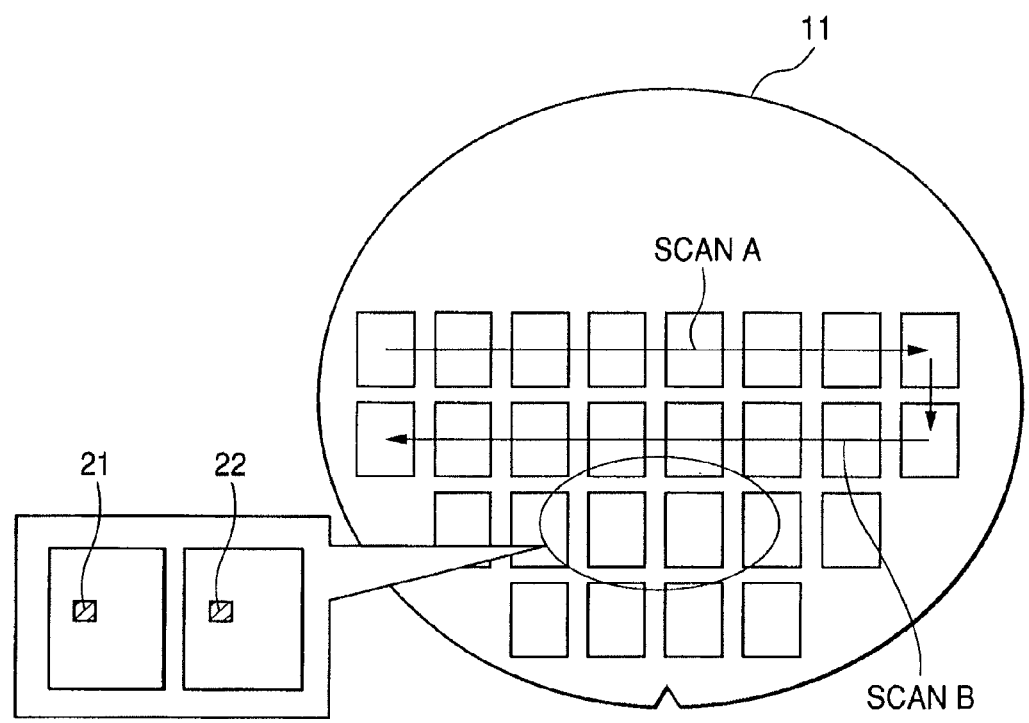
FIG. 2 is a plan view illustrating a semiconductor wafer as a target substrate.

As shown in FIG. 2, a large number of chips, each of which is expected to have the same pattern, are regularly arranged in rows on the semiconductor wafer 11 that is a target substrate. The image comparison unit 109 compares two images on two chips that are adjacent to each other, each of the two images being located at the same position on each of the two chips. For example, the image comparison unit 109 compares an image corresponding to an area 21 on a chip with an image corresponding to an area 22 on its adjacent chip shown in FIG. 2, and thereby detects, as a defect, part in which there is a difference between both of the images.

If its workings are described, the total control unit 15 successively moves the semiconductor wafer 11 as a target substrate by use of the stage 12, for example, in a direction opposite to a scan A direction shown in FIG. 2. In synchronization with the successive move of the stage 12, the detector 13 successively detects an optical image of the target substrate 11 in the scan A direction by use of the image sensor 104, and then captures an image of the chip. The image sensor 104 of the detector 13 outputs the inputted signal to the image processor 14.

In the image processor 14, the AD converter 105 converts the inputted analog signal into a digital signal, and then the preprocessor 106 performs shading correction, darkness level correction, and the like. Into the displacement detector 108, the following two signals are inputted as a set: an image signal (detected image signal) of a chip to be inspected which is output from the preprocessor 106; and an image signal delayed by a period of time during which the stage moves through the distance between chips, the image signal being inputted from the delay memory 107, that is to say, an image signal of a chip just before the chip to be inspected (reference image signal).

The displacement detector 108 calculates the amount of displacement by a pixel unit or less. The displacement is caused by, for example, vibrations of the stage during the move between the two images that are inputted in succession. At this time, although the detected image signal and the reference image signal are inputted in succession, the amount of displacement is successively calculated on a processing unit basis; in this case, the processing unit is a specific length.

The image comparison unit 109 uses the calculated amount of displacement to align the images, and then compares the detected image f (x, y) and the reference image g (x, y), which have been aligned. The image comparison unit 109 thereby outputs, as a defect candidate, an area whose difference value sub (x, y) is larger than the specific threshold value Th.

The feature extraction unit 110 edits each of defect candidates; for example, erasing a small defect candidate as a noise, merging adjacent defect candidates as one defect, and the like. Then, the feature extraction unit 110 calculates features such as a position, the area, and the size, in a wafer, and other features (a brightness value (a gray-scale value) and a brightness shape) used for the classification of defects.

The defect classification unit 111 classifies the defects using classification conditions set beforehand by the classification condition setting unit 116, and then outputs class information of each defect. The information is stored in the storage device 112. Further, the information is presented to users through the user interface 113.

Figure 3:
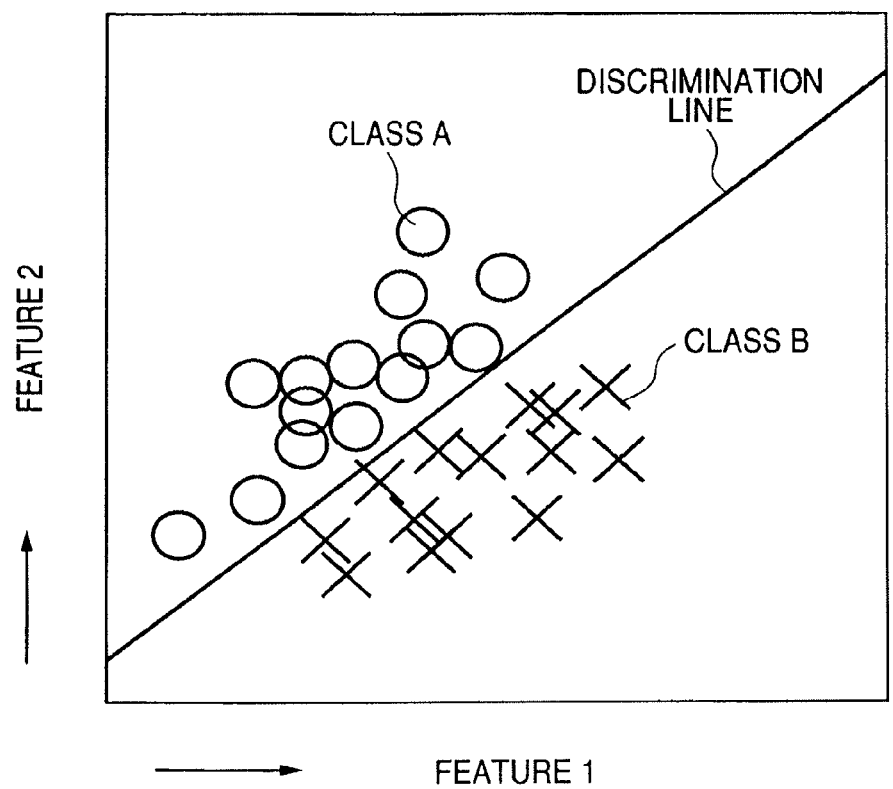
FIG. 3 is a diagram illustrating one embodiment of a classification method used in a visual inspection apparatus.
Figure 4:
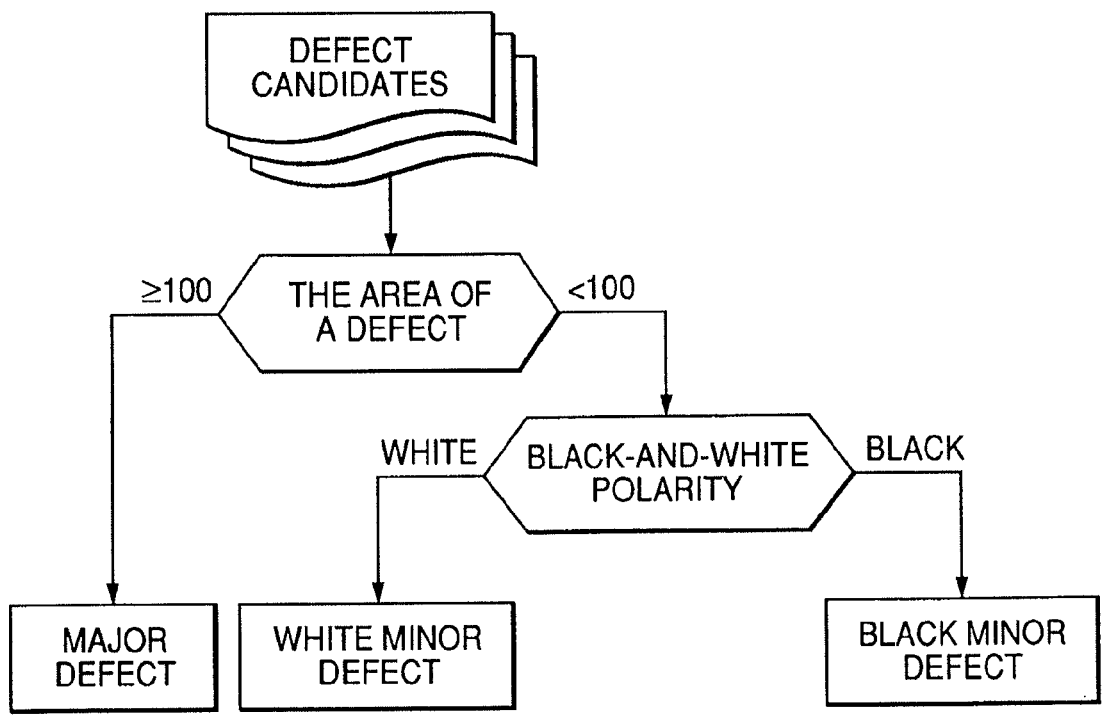
FIG. 4 is a diagram illustrating another embodiment of a classification method used in a visual inspection apparatus.

As a defect classification method carried out by the defect classification unit 111, it is thought that, for example, as shown in FIG. 3, defects are classified according to a discrimination line which is set on the basis of a scatter diagram illustrating two-dimensional features. In addition, as shown in FIG. 4, there is also a method in which defects are classified according to class decision rules described with if-then-else. In this case, decision rules are expressed by threshold values for features. In an example shown in FIG. 4, first of all, attention is paid to the area of a defect. If the area is 100 or more, the defect is classified as a major defect. On the other hand, if the area is smaller than 100, attention is next paid to black-and-white polarity that is a brightness value of the defect. If the black-and-white polarity is white, the defect is classified as a white defect, whereas if the black-and-white polarity is black, the defect is classified as a black defect. Besides the above methods, for example, there is a method in which a defect is classified into a training defect class whose distance on feature space is the shortest; and there is also a method in which feature distribution of each defect class is estimated on the basis of training data, and then a defect is classified into a class whose occurrence probability of a feature of the defect to be classified is the highest.

Next, review defect sampling performed by the defect sampling unit 115, or the like, and classification condition settings performed in the classification condition setting unit 116, or the like, according to the present invention, will be described with reference to FIGS. 5 through 7. The review defect sampling and the classification condition settings are performed with the objective of setting as training data (teaching data) of classification conditions on the basis of position coordinate information, and features, of each of a large number of defects. Here, the large number of defects are collected beforehand from the feature extraction unit 110 and are then stored in the storage device 112 by the total control unit (collection unit) 15.

Figure 5A:
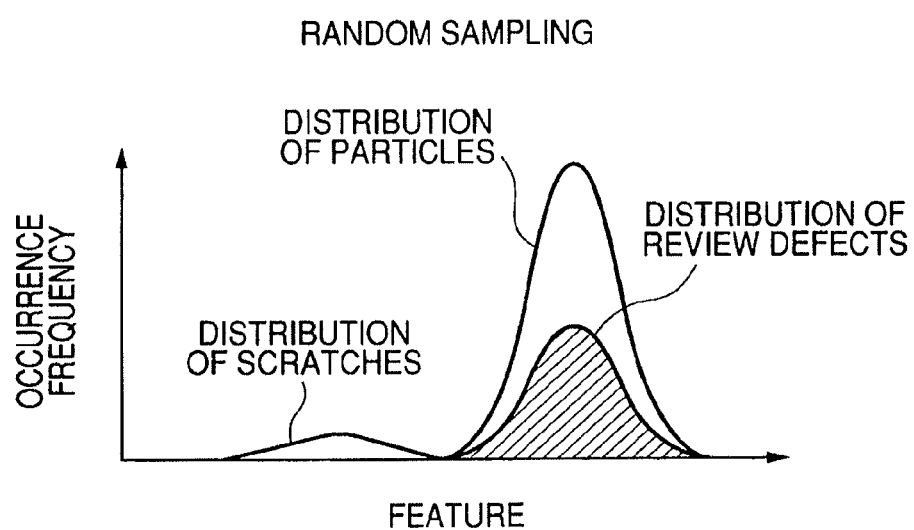
FIG. 5A is a graph illustrating the result of random sampling performed in a case where defect features are one-dimensional.
Figure 5B:
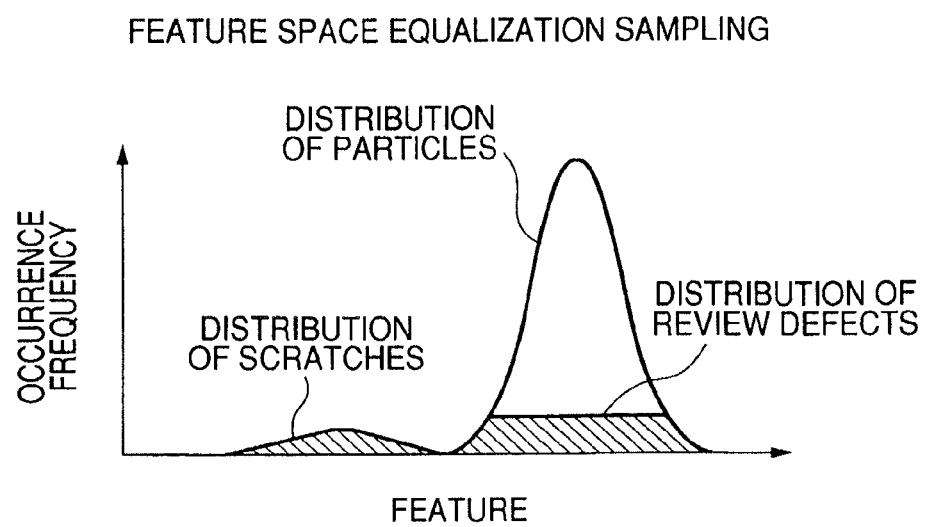
FIG. 5B is a graph illustrating the result of feature space equalization sampling performed in a case where defect features are one-dimensional.
Figure 6:
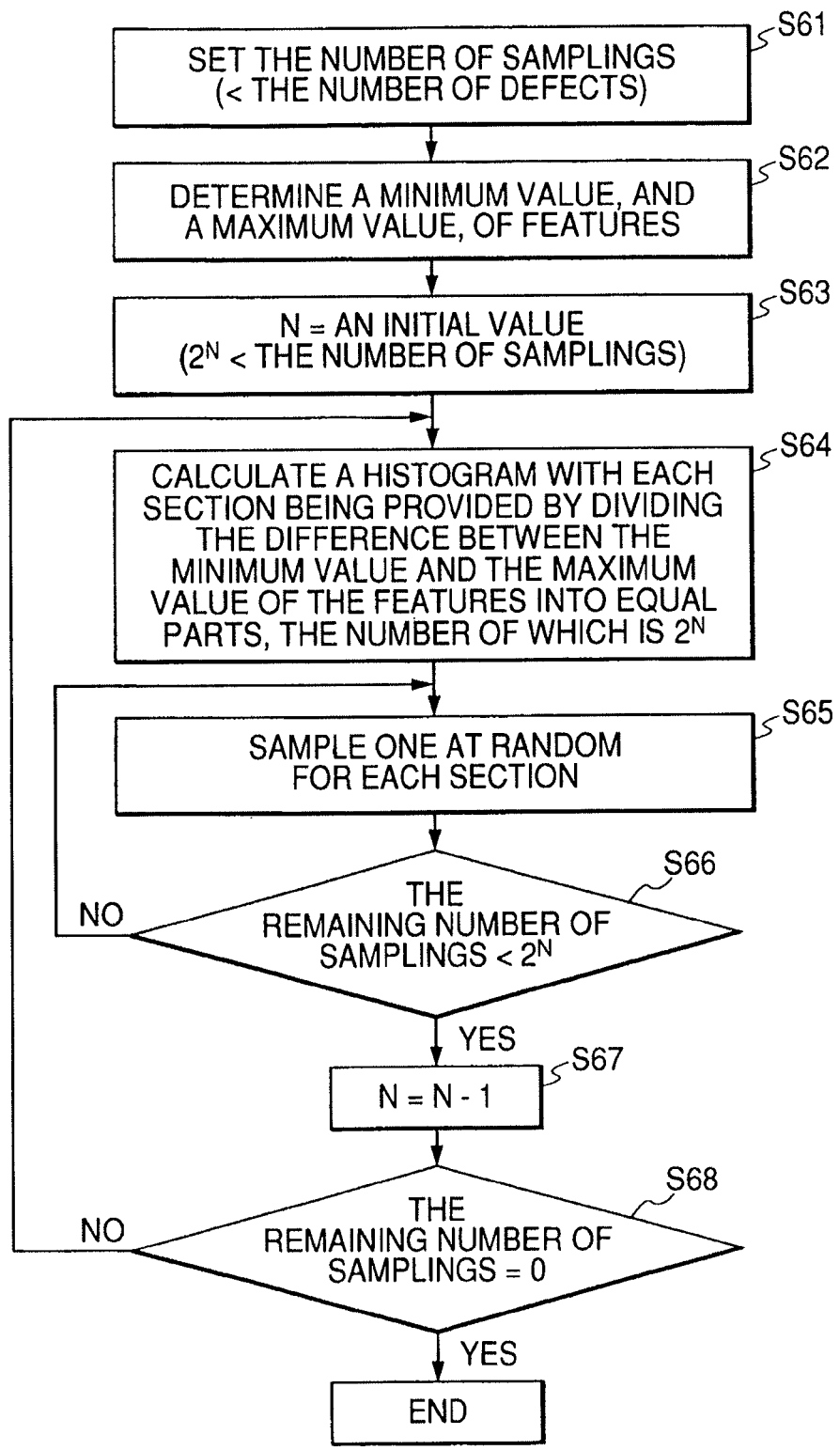
FIG. 6 is a flowchart illustrating the process flow of a defect sampling method according to a first embodiment.

FIGS. 5A, 5B are diagrams each illustrating a defect sampling method according to the present invention with a case where features are one-dimensional being taken as an example. In each of FIGS. 5A, 5B, a histogram whose horizontal axis indicates features, and whose vertical axis indicates the occurrence frequency, is shown. Here, it is assumed that defects include particles and scratches, and that the defects have normal distribution as shown in the figures. However, in actuality, it is not possible to discriminate between the particles and the scratches before reviewing.

FIG. 5A shows the result of random sampling. In the case of the random sampling, the distribution of review defects keeps the original occurrence ratio. Accordingly, the result is as shown with oblique lines in FIG. 5A. To be more specific, if the original occurrence frequency is biased, only one kind of defects (particles) will be mainly reviewed.

For this reason, according to the present invention, as shown with oblique lines in FIG. 5B, by performing sampling so that the distribution of review defects becomes as uniform as possible, it becomes possible to review the other kind of defects (scratches). This sampling technique shown in FIG. 5B will be hereinafter called feature space equalization sampling.

Next, a process flow of how to perform the feature space equalization sampling according to the present invention will be described with reference to FIG. 6. First of all, for example, using the user interface 113, the number of samplings (that is to say, the number of reviews) which is smaller than the number of defects is inputted into the defect sampling unit 115 so that the number of samplings is set (S61). At this time, if the number of reviews (the number of samplings) which has been set is larger than the number of defects that has been extracted and then has been stored in the storage device 112 by the feature extraction unit 110, all defects have only to be reviewed. Accordingly, the defect sampling part 115 judges that sampling is not required. Therefore, if sampling information including defect IDs and position coordinates over all defects stored in the storage device 112 are output as a file to, for example, the storage device 112, it is possible to provide the review tool 1103 with the sampling information.

Next, on the basis of features of all defects extracted by the feature extraction unit 110, the defect sampling unit 115 determines a range in which the features are distributed (in other words, a minimum value and a maximum value) (S62). Next, the defect sampling unit 115 determines an appropriate initial value of N such that 2 to the Nth power becomes smaller than the number of samplings which has been set (S63).

Next, the defect sampling unit 115 calculates a histogram with each section (the width is W) being provided by dividing the difference between the minimum value and the maximum value of the determined features into equal parts, the number of which is 2 to the Nth power (S64). At this time, the defect sampling unit 115 stores which defect (defect IDs) included in each section. Next, on the basis of the stored defect IDs included in each section, one is sampled at random for each section (the width is W) except section in where sampling defect doesn't become to exist (S65). Then, a judgment is made as to whether or not the remaining number of samplings is larger than 2 to the Nth power (S66). If the remaining number of samplings is larger than 2 to the Nth power, the step S65 is repeated.

As a result of the steps described above, until the remaining number of samplings becomes smaller than 2 to the Nth power, sampling can be equally performed at random for each of sections where section in where the sampling defect doesn't become to exist is excepted from all of the sections (each having the width W), each of which is provided by dividing a range in which the features are distributed (the difference between the minimum value and the maximum value) into equal parts, the number of which is 2 to the Nth power.

Next, if it is judged in the step S66 that the remaining number of samplings becomes smaller than 2 to the Nth power, N is decremented by one, and the width of a section to be sampled is doubled (2 W) (S67). Next, a judgment is made as to whether or not the remaining number of samplings is 0 (S68). If the remaining number of samplings is not 0, the process returns to the step S64 where the above range is divided into equal parts so that each of the equal parts has the doubled width (2 W), and then the histogram is recalculated (S64). At this time, which defect (defect IDs) of remaining defects being included in each section (the width is 2 W) is stored. Incidentally, the histogram can be easily recalculated because what is required is only to combine two sections of the original histogram into one section.

Next, on the basis of the remaining defect IDs included in each section (the width is 2 W), which have been stored, one is sampled at random for each of the sections (each having the width 2 W) where section in where the sampling remaining defect doesn't become to exist is excepted (S65). Then, a judgment is made as to whether or not the remaining number of samplings is larger than 2 to the (N−1)th power (S66). If the remaining number of samplings is larger than 2 to the (N−1)th power, the step S65 is repeated. If the remaining number of samplings is smaller than 2 to the (N−1)th power, N is further decremented by one, and the width of a section to be sampled is doubled again (4 W) (S67). Then, the steps S64 through S67 are repeated until the remaining number of samplings becomes 0. The sampling is completed at the point of time when the remaining number of samplings becomes 0.

As a result of the steps described above, the width of each equal part into which the feature distribution range is divided is doubled, quadrupled, and the like, until the remaining number of samplings becomes 0. This makes it possible to perform sampling substantially equally, and at random, for each of sections where section in where the sampling remaining defect doesn't become to exist is excepted. As a matter of course, after the second execution of the S65, defect that has not yet been sampled is targeted.

Incidentally, the defect sampling unit 115 used in the above-mentioned classification condition settings is configured to create a plurality of one-dimensional feature histograms as defect feature distribution, and to display the plurality of created one-dimensional feature histograms on the user interface 113, and then to select a desired one-dimensional feature histogram from among the plurality of displayed one-dimensional feature histograms.

Figure 7:
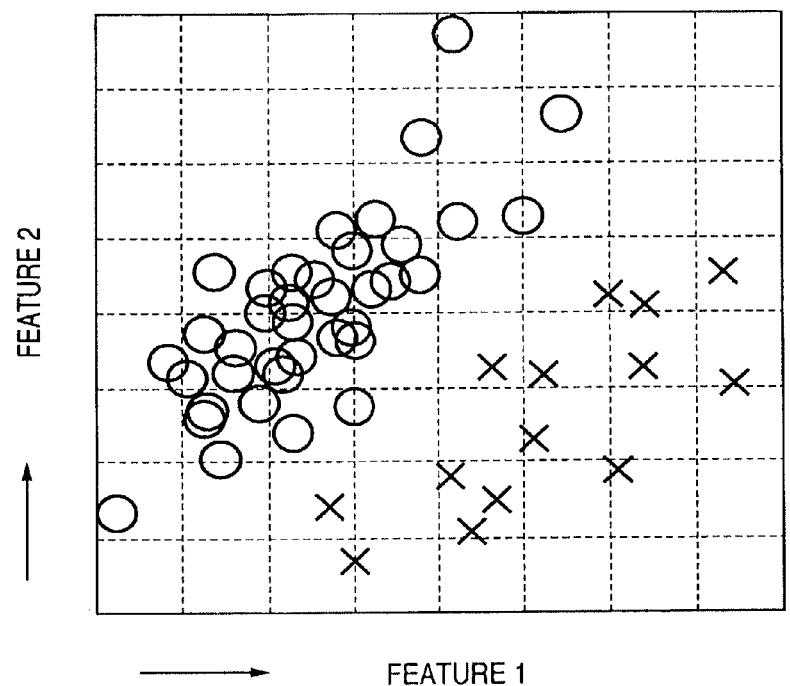
FIG. 7 is a diagram illustrating an embodiment of a defect sampling method in which features are two-dimensional.

In addition, if features of defects over all defects extracted by the feature extraction unit 110 are two-dimensional, a scatter diagram as shown in FIG. 7 is adopted. In this case, a feature distribution range is divided into cells of a lattice, and defects included in each cell are examined in advance. If the lattice is divided into cells, the number of which is 2 to the Nth power, such as 2×2, 4×4, 8×8, 16×16, . . . , then by using the same processing as that in the case of the one-dimensional features, the number of review defects (the number of samplings) included in each cell of the lattice can be made substantially equal with cells of the lattice where cell of the lattice in where the sampling defect doesn't become to exist is excepted. It is more preferable to provide, before the step S65, a step of counting existing sampling defects in each scale (each section, or each cell of the lattice, into which the lattice is divided by 2 to the Nth power) for adjustment.

Moreover, if features of defects over all defects extracted by the feature extraction unit 110 are three-dimensional or more, the similar processing can also be used by defining a multidimensional lattice. However, because the number of cells of the lattice increases, calculation becomes complicated. Accordingly, the three dimensions or more are reduced to two dimensions by use of a multivariate analysis technique such as the K-L (Karhunen-Loeve) expansion and self-organizing mapping, and then the similar processing is performed. Further, it may also be so configured that scatter diagrams are displayed with all combinations of two features, and then a selection is made from among them.

To be more specific, the defect sampling unit 115 used in the classification condition settings creates a plurality of feature scatter diagrams as the defect feature distribution, and displays the plurality of created feature scatter diagrams on the user interface 113, and then selects the desired two-dimensional feature space from among the plurality of displayed feature scatter diagrams. Here, the desired two-dimensional feature space may also be space into which the three-dimensional feature space or more is converted into two-dimensional feature space by compression.

Additionally, as described above, it may also be so configured that all features are displayed using histograms, and that one of the histograms is then selected from among them so as to perform the feature space equalization sampling for one dimension.

In all of the above methods, after inspection, according to an instruction from the user interface 113, the defect sampling unit 115 performs sampling of review defects on the basis of feature data corresponding to the number of samplings and defect IDs that are inputted from, for example, the total control unit 15. The defect sampling unit 115 then outputs, as sampling information, a file containing defect IDs and position coordinates of defects to be reviewed, to for example the storage device 112. As a result, the defect sampling unit 115 can provide the review tool 1103 with the review defect IDs and position coordinates thereof, which have been stored in the storage device 112, as sampling information. Incidentally, in the case of full automation, if the total control unit 15 sets beforehand a sampling mode for the defect sampling unit 115 on the basis of an inspection recipe, the defect sampling unit 115 may also perform the sampling immediately after the inspection.

Next, how the classification condition setting unit 116 sets classification conditions for the defect classification unit 111 through, for example, the total control unit 15 will be described. According to an instruction from the user interface 113, the classification condition setting unit 116 sets classification conditions in a state in which defect class information exists. The defect class information is acquired when the review tool 1103 reviews a corresponding wafer according to sampling information supplied from the defect sampling unit 115. If the defect class information does not exist, the classification condition settings are not performed. A classification condition setting method differs depending on a defect classification method. Incidentally, the classification condition setting unit 116 then receives defect IDs, defect class information, review defect images, and the like, which are the result of reviewing by the review tool 1103.

For example, as shown in FIG. 3, when classifying defects according to a discrimination line that is set in the two-dimensional feature space, the classification condition setting unit 116 displays a scatter diagram on the user interface 113 through the total control unit 15 by use of the defect class information of the defect IDs acquired from the review tool 1103, and by use of the feature information of the defect IDs extracted by the feature extraction unit 110. Then, for example, a straight line with inclination 1 is displayed. The inclination and intercepts are adjusted with cursor keys to determine the discrimination line, which is stored in the storage device 112.

Figure 8:
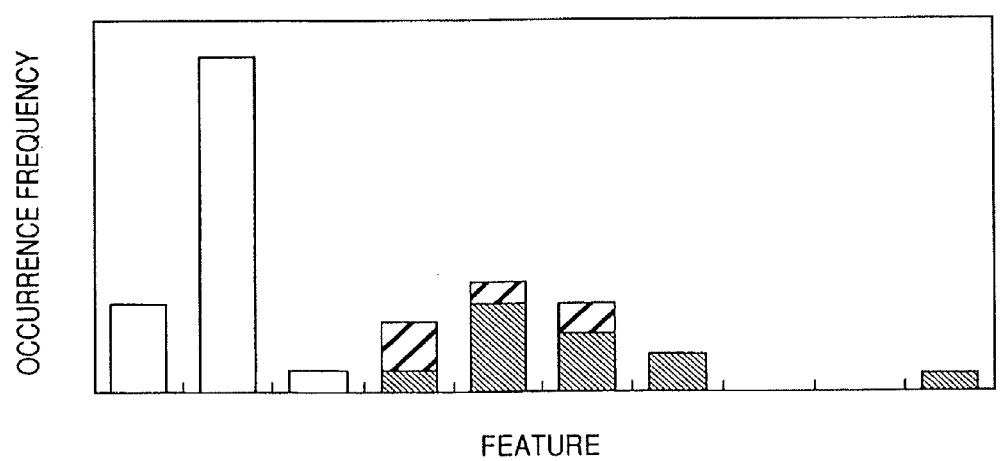
FIG. 8 is a diagram illustrating an embodiment of a histogram in which features are shown on a defect class basis.

In addition, as shown in FIG. 4, when classifying defects according to class decision rules described with if-then-else, the classification condition setting unit 116 displays a histogram as shown in FIG. 8 on the user interface 113 through the total control unit 15. In the histogram, for all features extracted by the feature extraction unit 110, different defect classes are expressed in different colors (the different defect classes may also be acquired from the review tool 1103 if necessary).

While viewing the displayed histogram, a user manually describes a class decision rule, and then inputs the class decision rule into the total control unit 15 through the user interface 113. The total control unit 15 provides the classification condition setting unit 116 with the described class decision rule as classification conditions. Moreover, the user interface 113 is configured to allow users to use button operation for selection of a feature amount, selection of a defect class name, setting of a threshold value by moving a boarder line in the histogram, and selection between (larger than or equal to) and (smaller than or equal to). According to the input by the user, the classification condition setting unit 116 creates class decision rules as classification conditions.

Further, on the basis of position coordinates, feature information, defect images, and the like, of defect IDs extracted by the feature extraction unit 110, and on the basis of defect IDs, defect class information, review defect images, and the like, which are acquired from the review tool 1103, the classification condition setting unit 116 can also automatically create class decision rules as classification conditions by use of, for example, the decision tree algorithm described in Japanese Patent Laid-Open No. 2004-47939.

In addition, if a learning type classification technique is adopted, the classification condition setting unit 116 follows the technique to learn, as training samples (teaching samples), defect class information acquired from the review tool 1103 and defect feature information extracted by the feature extraction unit 110, and then outputs, as a file, classification conditions to the storage device 112. Here, when the distribution of defect class is estimated on the basis of the training samples, as shown in FIG. 5B, distribution that differs from true distribution is determined. If it is thought that this will exert a bad influence upon the classification performance, the bad influence can be avoided by giving weight to the training samples using (the number of defects existing in a feature section to which the training samples belong/the number of training in the section) before learning.

Second Embodiment

Next, a second embodiment of a visual inspection method and an apparatus according to the present invention will be described with reference to FIG. 9. A point of difference between the first and second embodiments is that a processing method carried out by the defect sampling unit 115 in the second embodiment differs from that in the first embodiment. In the first embodiment, sections are full automatically and semiautomatically set in the feature space. However, sections are manually set in the second embodiment. This method will be described as below.

According to an instruction from the user interface 113 after inspection, the defect sampling unit 115 inputs feature data of each defect corresponding to each defect ID that has been extracted and then has been stored in the storage device 112 by the feature extraction unit 110. Next, the defect sampling unit 115 creates a histogram illustrating features of defects, and then displays the histogram on the user interface 113.

Figure 9:
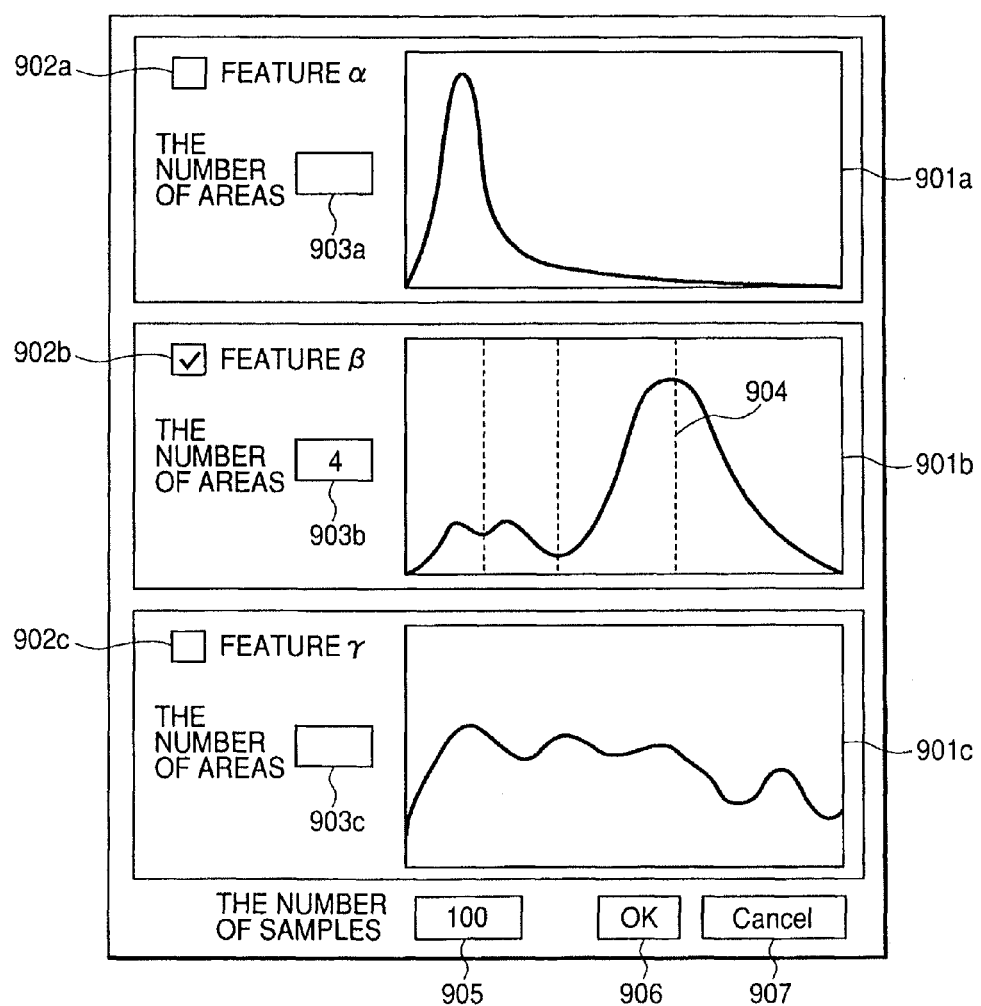
FIG. 9 is a diagram illustrating an embodiment of a GUI through which feature sections are manually set according to a defect sampling method.

FIG. 9 illustrates an example of a display screen displayed in a case where the number of defect features is three. 901a, 901b, 901c are histograms illustrating defect features α, β, γ respectively. The horizontal axis indicates features, whereas the vertical axis indicates the occurrence frequency. 902a, 902b, 902c are check buttons, each of which indicates whether or not a feature of each defect is selected. Here, it is assumed that only one can be selected. The user selects any one of the defect features by clicking a button.

In the example shown in the figure, the defect feature β is selected. In this manner, it is desirable to select a feature whose distribution has a plurality of peaks. If a defect feature is selected, a corresponding area count input box 903b is activated. 2 is set as a default value; and a borderline 904 is displayed at a position at which the histogram is divided into two equal parts. If a value inputted into the area count input box 903b changes, the number of displayed borderlines 904 also changes. Users can freely determine a feature section of defects by dragging and moving the borderline 904. By inputting the number of samples (the number of samplings that is the number of reviews) into a sample count input box 905 before an OK button 906 is clicked, the defect sampling unit 115 performs sampling of review defects so that the number of samples in each section becomes roughly equal with sections where section in where the sampling defect, each of which includes no defect to be sampled. Then, the defect sampling unit 115 outputs, as a file, defect IDs to for example the storage device 112.

To be more specific, the defect sampling unit 115 used in the classification condition settings executes the steps of: creating, as the defect feature distribution, a plurality of feature histograms over a large number of defects; displaying the plurality of created feature histograms on the user interface 113; selecting one feature histogram from among the plurality of displayed feature histograms; and performing sampling so that the number of samples from the feature section, which has been freely set in the one selected feature histogram, becomes roughly equal with sections where section in where the sampling defect doesn't become to exist is excepted. Then, if a user wants to end the processing without performing the sampling, the user clicks a cancel button 907.

In the visual inspection apparatus, if not only feature data of defects extracted by the feature extraction unit 110 but also inspection images of the defects are stored in the storage device 112, when the defect sampling unit 115 samples review defects so that the number of samples in each section becomes roughly equal with sections where section in where the sampling defect doesn't become to exist is excepted, it becomes possible to support a judgment made by the user using the defect inspection images. In such a case, when any one of defect features is selected by clicking one of the check buttons 902, the defect inspection images are displayed by sorting with values of the defect features. Incidentally, when the inspection images of defects are displayed, the divisions of the sections based on the borderlines 904 shown in the histogram are also made to recognize.

Third Embodiment

Next, a third embodiment of a visual inspection method and an apparatus according to the present invention will be described with reference to FIGS. 10A, 10B, 10C. Paying attention to the third embodiment, a point of difference between the first and second embodiments is that a processing method carried out by the defect sampling unit 115 in the third embodiment differs from that in the first and second embodiments. In the first and second embodiments, sampling is performed on the basis of defect features based on detected image information. However, in the third embodiment, sampling is performed by use of position information of defects in combination with the above-mentioned defect features.

First of all, a first method in the third embodiment will be described. In the first method, the defect position information used in combination with the defect features is the shortest distance from the adjacent defect, the local defect density and the like, calculated by using, for example, the method described in "Visual inspection technique using defect point sampling technology" the 13th workshop on automation of visual inspection, pp. 99-104 (December, 2001) on the basis of coordinates of all defects after inspection. Here, the first method is a method in which, in combination with the defect features based on the above image information, defect position information including the shortest distance from the adjacent defect and the local defect density is used for sampling with the number of dimensions of the defect features being increased.

Next, a second method in the third embodiment will be described. As far as the second method is concerned, processing method carried out by the classification condition setting unit 116 is also different from that described in the first and second embodiments.

To be more specific, in the second method, first of all, on the basis of position coordinates of defects extracted by the feature extraction unit 110, the defect sampling unit 115 analyzes how the defects are distributed, and thereby detects densely located defects, linear defects, and circular arc shaped defects as shown in wafer maps in FIGS. 10A, 10B, 10C, respectively. In this case, the analyzing method of the defect distribution state uses the method described in Japanese Patent Laid-Open No. 2003-59984 or Japanese Patent Laid-Open No. 2004-117229. The densely located defects are detected by grouping together each defect whose distance from another defect is shorter than a predetermined threshold value. The linear defects are defects that are densely distributed in the shape of a straight line; and the circular arc shaped defects are defects that are densely distributed in the shape of a circular arc.

Such characteristic distribution is generically called a cluster. It is empirically understood that defects constituting a cluster may also be considered to belong to the same kind of defects. For this reason, the defect sampling unit 115 samples a few defects from each cluster to check (confirm) defect class (defect kind), and then presents IDs and position coordinates of the sampled review defect onto the review tool 1103, and the review tool 1103 reviews the presented defects. In addition, for defects that do not constitute a cluster, the defect sampling unit 115 samples the defects by the method described in the first embodiment or in the second embodiment. In this case, the defects constituting the cluster are not included in the calculation of the histogram.

Next, the classification condition setting unit 116 regards all of the defects constituting the cluster as defects in the same class so that samples which have not been reviewed are also used as training data (teaching data). In another case, the defects constituting the cluster are excluded as defects belonging to a particular class, and the reviewed samples are also not used as training samples (teaching samples). The other points are similar to the first and second embodiments.

Fourth Embodiment

Next, a fourth embodiment of a visual inspection method and an apparatus according to the present invention will be described with reference to FIGS. 11, 12. In the first, second and third embodiments, the visual inspection apparatus is configured to include the defect sampling unit 115 and the classification condition setting unit 116. However, in the fourth embodiment, these means 115, 116 are separately configured as a classification condition setting apparatus.

FIG. 11 is a diagram illustrating a system configuration for the above case. The system configuration includes: a visual inspection apparatus 1101; a classification condition setting apparatus (classification condition setting means having a collection unit for collecting position coordinate information, and features, of defects over a large number of defects to store them in a storage device, the defects being acquired from the feature extraction unit 110 of the visual inspection apparatus 1101) 1102; and a review tool 1103. Each arrow indicates data input/output.

The classification condition setting apparatus 1102 comprises the collection unit (not illustrated), a defect sampling unit 115, and a classification condition setting unit 116. The defect sampling unit 115 includes a collection unit (not illustrated) for inputting and storing defect ID, position coordinates and feature data which correspond to the defect ID, being output from the visual inspection apparatus 1101, and an inspection image although it is not indispensable. Sampling of review defects is performed by the same method as any of the methods described in the first, second and third embodiments; and defect IDs, and position coordinates, of the review defects are output.

The review tool 1103 performs reviewing according to the position coordinates of the review defects, and then automatically classifies the defects to output defect classes and review images, which are associated with defect IDs. The classification condition setting unit 116 is inputted the defect classes of the review defects by input means (including a bus and Internet), and learns the defect classes as training samples in combination with corresponding feature data, and then outputs classification conditions to the defect classification unit 111 of the visual inspection apparatus 1101.

The classification condition setting unit 116 can also be configured to input review images, and to allow manual classification. According to this configuration, even if the review tool 1103 only acquires images and does not classify defects, classification condition settings become possible.

FIG. 12 is a diagram illustrating a defect training GUI for displaying review images, and for manually classifying defects. Maps, which show defect positions in a wafer and a die, are displayed in a wafer map display window 1201 and a die map display window 1202 respectively. In an inspection image display window 1203, inspection images are displayed in each defect class and order of defect IDs. All defects are displayed without duplication in any of defect classes or in "unclassified". By dragging and dropping an image, it is possible to train (teach) a defect class of a corresponding defect. What are displayed in an inspection information detail display window 1204 includes: a defect image 1205 and a reference image 1206 that have been acquired for a selected defect by the inspection apparatus; a defect image 1207 and a reference image 1208 that have been acquired by the review tool; and a features list 1209. A defect is selected by any of the following operation: clicking a defect point on the wafer map; clicking a defect point on the die map; and clicking an inspection image in the inspection image display window 1203.

According to this method, it is also possible to train a defect class of an unreviewed defect on the basis of an inspection image. If a judgment cannot be made, the defect may be left in the "unclassified". Therefore, it is possible to increase the number of training samples. As a result, correct classification condition settings become possible.

The present invention can be applied to a visual inspection apparatus having an automatic defect classification function targeted for thin film devices including a semiconductor wafer, TFT, and a photo mask.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A visual inspection method for performing a visual inspection of semiconductor devices using a computer system provided with an image detector unit, an image processor unit and a display unit, the visual inspection method comprising:
   a classification condition setting step of setting classification conditions beforehand;
   a defect candidate detection step of detecting defect candidates by using inspection images acquired by imaging a target substrate, via the image detector unit, and calculating features of the defect candidates; and
   a defect candidate classification step of classifying the defect candidates in accordance with the classification conditions set beforehand in the classification condition setting step using the features of the defect candidates calculated in the defect candidate detection step, via the imaging processor unit,
   wherein said classification condition setting step further comprises:
   a collection step of detecting a large number of defect candidates as review defects by using images acquired by imaging a sample substrate, which are different from the inspection images acquired at the defect candidate detection step, and collecting calculated features of each defect candidate over the large number of defect candidates, and collecting calculated features of each defect candidate over the large number of defect candidates so as to store collected features of each defect candidate;
   a defect sampling step of creating a defect feature distribution indicating a defect occurrence distribution based on the collected features of each defect candidate over the large number of defect candidates in the collection step, and performing sampling of review defects based on the defect feature distribution; and
   a review step of distinguishing at least whether a defect candidate is a defect or not to a plurality of review defects by reviewing the review defects sampled in the defect sampling step,
   wherein results of distinctions of the review defects provided in the reviewing step correspondence with features of the review defects detected in the collection step, are set as training data of the classification conditions.

2. The visual inspection method according to claim 1, wherein in said defect sampling step, a desired one-dimensional feature histogram over a large number of defect candidates is created as the defect feature distribution, and the sampling is performed so that, in the created one-dimensional feature histogram, a number of samples from each of sections into which the desired one-dimensional feature histogram is divided with respect to the features becomes roughly equal with sections in which no sampling defect candidate is expected.

3. The visual inspection method according to claim 2, wherein said defect sampling step comprises:
   creating a plurality of one-dimensional feature histograms as the defect feature distribution;
   providing a visual display of the plurality of one-dimensional feature histograms on the display unit; and
   selecting the desired one-dimensional feature histogram from among the plurality of one-dimensional feature histograms displayed on the display unit.

4. The visual inspection method according to claim 1, wherein in said defect sampling step, a desired two-dimensional feature space over a large number of defect candidates is created as the defect feature distribution, and the sampling is performed so that in the created two-dimensional feature space, which is divided into cells of a lattice with respect to the features, a number of samples included in each lattice becomes roughly equal with cells of the lattice where a cell of the lattice in where the sampling defect candidate does not exist is expected.

5. The visual inspection method according to claim 4, wherein said defect sampling step comprises:
   creating a plurality of feature scatter diagrams as the defect feature distribution;
   displaying the plurality of features scatter diagrams on the display unit; and
   selecting the desired two-dimensional feature space from among the plurality of feature scatter diagrams displayed on the display unit.

6. The visual inspection method according to claim 4, wherein said two-dimensional feature space is space into which three-dimensional feature space or more is covered into two-dimensional feature space by compression.

7. The visual inspection method according to claim 1, wherein said defect sampling step comprises:
   creating a plurality of feature histograms over a large number of defect candidates as the defect feature distribution;
   providing a visual display of the plurality of feature histograms on the display unit; and
   selecting one feature histogram from among the plurality of feature histograms displayed on the display unit, and performing sampling so that a number of samples from each of feature sections which have been freely set in said selected one of the feature histograms becomes roughly equal with feature sections where feature section in which the sampling defect candidates does not exist is expected.

8. The visual inspection method according to claim 1, wherein in said collection step, the collected features of each defect candidate include features based on defect candidate images, and features based on positions coordinated of defect candidates.

9. A visual inspection apparatus for performing a visual inspection of semiconductor devices, comprising:
   an image detector unit,
   an image processor unit; and
   a display unit,
   wherein said image processor unit includes:
   a classification condition setting section for setting classification conditions;
   a defect candidate detection section for detecting defect candidates by using inspection images acquired by imaging a target substrate with said image detector unit, and calculating features of the detected defect candidates; and
   a defect candidate classification section for classifying the defect candidates in accordance with the classification conditions set by the classification condition setting section using the features of the defect candidates calculated in the defect candidate detection section, wherein said classification condition setting section further comprises:

a collection part for detecting a large number of defect candidates as review defects by using images acquired by imaging a sample substrate with said image detector unit, which are different from the inspection images treated by the defect candidate detection section, and collecting calculated features of each defect candidate over the large number of defect candidates to store collected features of each defect candidates;

a defect sampling part for creating a defect feature distribution indicating a defect occurrence distribution based on the collected features of each defect candidate over the large number of defect candidates collected by the collection part, and sampling the review defects based on the defect feature distribution; and a review part for distinguishing at least whether a defect candidate is a defect or not to a plurality of review defects by reviewing the review defects sampled in the defect sampling part, wherein said classification condition setting section sets training data of the classification conditions based on results of distinctions of the review defects provided by the review part correspondence with features of the review defects detected in the collection part.

10. The visual inspection apparatus according to claim 9, wherein said defect sampling part creates a desired one-dimensional feature histogram over the large number of defect candidates as the defect feature distribution, and samples the review defects so that, in the created desired one-dimensional feature histogram, a number of samples from each of sections into which the desired one-dimensional feature histogram is divided with respect to the features becomes roughly equal with sections in which no sampling defect candidate is expected.

11. The visual inspection apparatus according to claim 10, wherein said defect sampling part comprising:

a one-dimensional feature histogram creation portion for creating a plurality of one-dimensional feature histograms as the defect feature distribution;

a visual display providing portion for providing a visual display of the plurality of one-dimensional feature histograms of the display unit; and a selecting portion for selecting the desired one-dimensional feature histogram from among the plurality of one-dimensional feature histograms displayed on the display unit.

12. The visual inspection apparatus according to claim 9, wherein said defect sampling part creates a desired two-dimensional feature space over the large number of defect candidates as the defect feature distribution, and samples the review defects so that, in the created two-dimensional feature space, which is divided into cells of a lattice with respect to the features, a number of samples included in each lattice becomes roughly equal with cells of the lattice where a cell of the lattice in where the sampling defect candidate does not exist is expected.

13. The visual inspection apparatus according to claim 12, wherein said defect sampling part comprises:

a feature scatter diagram creating portion for creating a plurality of feature scatter diagrams as the defect feature distribution;

a display image data sending portion for sending image data of the plurality of features scatter diagrams for a visual display on the display unit; and a desired two-dimensional feature space selecting portion for selecting the desired two-dimensional feature space from among the plurality of feature scatter diagrams displayed on the display unit.

14. The visual inspection apparatus according to claim 12, wherein said defect sampling part creates said desired two-dimensional feature space into which three-dimensional feature space or more is covered into two-dimensional feature space by compression.

15. The visual inspection apparatus according to claim 9, wherein said defect sampling part comprises:

a feature histogram creating portion for creating a plurality of feature histograms over a large number of defect candidates as the defect feature distribution;

a feature histogram data providing portion providing the plurality of feature histograms data to the display unit for displaying; and a feature histogram selecting portion for selecting one feature histogram from among the plurality of feature histograms designated on the display unit on which the plurality of feature histograms are displayed, and performing sampling so that a number of samples from each of feature sections which have been freely set in said selected one of the feature histograms becomes roughly equal with feature sections where feature section in which the sampling defect candidates does not exist is expected.

16. The visual inspection apparatus according to claim 9, wherein said collection portion collects features of each defect candidate including features based on defect candidate images, and features based on positions coordinated of defect candidates.

* * * * *